(12) United States Patent
Okuda

(10) Patent No.: US 8,309,339 B2
(45) Date of Patent: Nov. 13, 2012

(54) ALKALINE PROTEASE

(75) Inventor: Mitsuyoshi Okuda, Haga-gun (JP)

(73) Assignee: Kao Corporation, Tokyo (JP)

( * ) Notice: Subject to any disclaimer, the term of this patent is extended or adjusted under 35 U.S.C. 154(b) by 505 days.

(21) Appl. No.: 12/522,419

(22) PCT Filed: Mar. 6, 2008

(86) PCT No.: PCT/JP2008/054562
§ 371 (c)(1),
(2), (4) Date: Jul. 8, 2009

(87) PCT Pub. No.: WO2008/111628
PCT Pub. Date: Sep. 18, 2008

(65) Prior Publication Data
US 2010/0184188 A1 Jul. 22, 2010

(30) Foreign Application Priority Data
Mar. 6, 2007 (JP) .................................. 2007-056022

(51) Int. Cl.
*C12N 9/48* (2006.01)
(52) U.S. Cl. ....................................................... 435/212
(58) Field of Classification Search .......................... None
See application file for complete search history.

(56) References Cited

U.S. PATENT DOCUMENTS

| | | | |
|---|---|---|---|
| 4,797,362 A | 1/1989 | Takeuchi et al. |
| 5,665,587 A | 9/1997 | Aaslyng et al. |
| 6,376,227 B1 | 4/2002 | Takaiwa et al. |
| 6,802,222 B2 | 10/2004 | Ishio et al. |
| 7,368,273 B2 | 5/2008 | Okuda et al. |
| 7,405,271 B2 | 7/2008 | Sato et al. |
| 7,429,642 B2 | 9/2008 | Okuda et al. |
| 7,473,544 B2 | 1/2009 | Okuda et al. |
| 2002/0064854 A1 | 5/2002 | Takaiwa et al. |
| 2003/0022351 A1 | 1/2003 | Hatada et al. |
| 2004/0002432 A1 | 1/2004 | Okuda et al. |
| 2004/0203129 A1 | 10/2004 | Hatada et al. |
| 2005/0026804 A1 | 2/2005 | Sato et al. |
| 2005/0214922 A1 | 9/2005 | Okuda et al. |
| 2006/0078978 A1 | 4/2006 | Okuda et al. |
| 2006/0105428 A1 | 5/2006 | Sato et al. |
| 2008/0177040 A1 | 7/2008 | Okuda et al. |

FOREIGN PATENT DOCUMENTS

| | | |
|---|---|---|
| EP | 1 029 920 A | 8/2000 |
| EP | 1 466 970 A | 10/2004 |
| EP | 1 645 632 A | 4/2006 |
| JP | 49-71191 A | 7/1974 |
| JP | 61-280268 A | 12/1986 |
| JP | 03191781 A | 8/1991 |
| JP | 2002-218989 | 8/2002 |
| JP | 2002-306176 | 10/2002 |
| JP | 3343115 B2 | 11/2002 |
| JP | 2003-125783 | 5/2003 |
| JP | 2004-122 | 1/2004 |
| JP | 2004-57195 | 2/2004 |
| JP | 2004-305175 | 11/2004 |
| JP | 2004-305176 | 11/2004 |
| JP | 2006-129865 | 5/2006 |
| WO | WO 88/01293 | 2/1988 |
| WO | WO 91/00334 | 1/1991 |
| WO | WO 91/00345 A1 | 1/1991 |
| WO | WO 98/56927 | 12/1998 |
| WO | WO 99/18218 | 4/1999 |

OTHER PUBLICATIONS

GenBank Acc# BAB21267.1 from Saeki et al, Biochem Biophys Res Commun. Dec. 20, 2000;279(2):313-9. Alignment with SEQ ID No. 2.*
Saeki et al, Biochem Biophys Res Commun. Dec. 20, 2000;279(2):313-9.*
Guo et al, Protein tolerance to random amino acid change. Proc Natl Acad Sci U S A. Jun. 22, 2004;101(25):9205-9210. Epub Jun 14, 2004.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
JP Office Action for JP 2007-056022, written on Jun. 29, 2012, Japanese Patent Office, Tokyo, Japan.
International Search Report mailed Aug. 8, 2008, for PCT/JP2008/054562, European Patent Office, The Netherlands.
Russell, AJ et al.,"Electrostatic effects on modification of charged groups in the active site cleft of subtilisin by protein engineering," J Mol Biol. 193(4): 803-813 (Feb. 1987).
Russell, AJ and AR Fersht, "Rational modification of enzyme catalysis by engineering surface charge," Nature 328(6130): 496-500 (Aug. 1987). Saeki, K., et al., "Novel oxidatively stable subtilisin-like serine proteases from alkaliphilic *Bacillus* spp.: enzymatic properties, sequences, and evolutionary relationships," Biochem Biophys Res Commun, 279(2): 313-9 (Dec. 2000).
Shirai, T. et al., "High-resolution crystal structure of M-protease: phylogeny aided analysis of the high-alkaline adaptation mechanism," Prot. Engineer. 10(6): 627-634 (Jun. 1997).
Thomas, PG et al. "Tailoring the pH dependence of enzyme catalysis using protein engineering," Nature 318, 375-376 (Nov. 1985).
Genbank Accession No. AB051423, *Bacillus* sp. KP43 PROF gene for protease, version AB051423.2, GI:20521154, complete cds, May 10, 2002.
Genbank Accession No. AB46402, *Bacillus* sp. D6 PROA gene for protease, version AB46402.1, GI:12381936, partial cds, Jun. 16, 2001.
Genbank Accession No. AB046404, *Bacillus* sp. Y PROC gene for protease, version AB046404.1, GI:12381940, partial cds, Jan. 23, 2001.

(Continued)

*Primary Examiner* — Sheridan Swope
(74) *Attorney, Agent, or Firm* — Sterne, Kessler, Goldstein & Fox P.L.L.C.

(57) ABSTRACT

It is an object of the present invention to provide alkaline proteases having industrially sufficient protein productivity and a significant detergency. In the alkaline proteases, the amino acid residues at (a) position 9, (b) position 49, (c) position 194, (d) position 212, (e) position 237, (f) position 245, (g) position 281, (h) position 313, (i) position 379 and (j) position 427 in SEQ ID NO: 2 are selected from the following amino acid residues; Position (a); glutamine, Position (b); glutamine, Position (c); lysine or arginine, Position (d); arginine, asparagine or glutamine, Position (e); asparagines, Position (f); asparagines. Position (g); arginine, Position (h); asparagines, Position (i); lysine, arginine, glutamic acid or aspartic acid, and Position (j); arginine.

11 Claims, No Drawings

OTHER PUBLICATIONS

Genbank Accession No. AB046405, *Bacillus* sp. SD521 PROD gene for protease, version AB046405.1, GI:12381942, partial cds, Jan. 23, 2001.

Genbank Accession No. AB046406, *Bacillus* sp. NV1 PROE gene for protease, version AB046406.1, GI:12381944, partial cds, Jan. 23, 2001.

Genbank Accession No. AB084155, *Bacillus* sp.KSM-9865 gene for protease, version AB084155.1, GI:34392386, complete cds, Sep. 2, 2003.

Dialog File 351, World Patents Index, Accession No. 5679121, English language abstract and patent family for JP 03191781 A, published Aug. 21, 1991.

Dialog File 351, World Patents Index, Accession No. 673535, English language abstract and patent family for JP 49-071191 A, published Jul. 10, 1974.

Dialog File 351, World Patents Index, Accession No. 3868757, English language abstract and patent family for JP 61-280268 A, published Dec. 10, 1986.

Dialog File 351, World Patents Index, Accession No. 12490206, English language patent family for JP 2002-18989 A, published Aug. 6, 2002 and for JP 2002-306176, published Oct. 22, 2002.

Dialog File 351, World Patents Index, Accession No. 13757582, English language patent family for JP 2003-125783 A, published May 7, 2003.

Dialog File 351, World Patents Index, Accession No. 13747877, English language patent family for JP 2004-000122 A, published Jan. 8, 2004 and for JP 2004-57195 A, published Feb. 26, 2004.

Dialog File 351, World Patents Index, Accession No. 14529366, English language patent family for JP 2004-305175 A, published Nov. 4, 2004.

Dialog File 351, World Patents Index, Accession No. 14529362, English language patent family for JP 2004-305176 A, published Nov. 4, 2004.

Dialog File 351, World Patents Index, Accession No. 15702417, English language patent family for JP 2006-129865, published May 25, 2006.

\* cited by examiner

ALKALINE PROTEASE

REFERENCE TO SEQUENCE LISTING SUBMITTED ELECTRONICALLY

The content of the electronically submitted substitute sequence listing, file name: SequenceListing.TXT; Size: 23,248 bytes; and Date of Creation: Nov. 9, 2009, filed herewith, is incorporated herein by reference in its entirety.

FIELD OF THE INVENTION

The present invention relates to alkaline proteases being effective as enzymes to be incorporated in detergents, and genes encoding the same.

BACKGROUND OF THE INVENTION

Proteases have been used in the industry for a long time. They are used in a variety of fields including detergents such as laundry detergents, fabric modifiers, leather processing agents, cosmetics, bath agents, food modifiers or medicines. Of these uses, proteases for detergents are industrially produced in the largest amount. Examples of proteases for detergents include Alcalase and Savinase (registered trademarks; Novozymes A/S), Maxacal (registered trademark; Genencor International Inc.), BLAP (registered trademark; Henkel KGaA), and KAP (Kao Corporation).

The purpose of incorporating protease into a detergent is to promote degradation of protein-based stains attached to clothing into low molecular Weight substances, and solubilization thereof by a surfactant. However, actual stains are complex stains which contain not only proteins but also a mixture of plural components such as organic substances and inorganic substances, for example, sebum-derived lipids and solid particles. Therefore, there is a demand for detergents having a significant detergency on such complex stains.

Based on this standpoint, the present inventors have found a few kinds of alkaline proteases, which retain a sufficient caseinolytic activity even in the presence of a high concentration of a fatty acid, exhibit a significant detergency on complex stains containing not only proteins but also sebum and the like weaved therewith, and have a molecular weight of approximately 43,000 (Patent Document 1). It is suggested that the aforementioned group of alkaline proteases are categorized to a novel subtilisin subfamily, unlike the conventionally known serine proteases typified by subtilisin derived from bacteria belonging to *Bacillus* sp., in terms of their molecular weights, primary structures, enzymatic properties, and, in particular, exhibiting extremely strong oxidant resistance (Nonpatent Literature 1).

The above group of alkaline proteases has a significant detergency under the conditions where sebum stains and the like are weaved with each other. Moreover, alkaline proteases having sufficient productive performances in addition to detergency remain in demand.

In general, an enzymatic activity changes in a pH-dependent manner because the enzyme has an amino acid residue having either a dissociable acidic group or a dissociable basic group, which is essential for the expression of the activity thereof, at the active site of the enzyme. Therefore, an attempt to artificially alter the pH-dependence of an enzymatic activity by altering a charged amino acid residue is one of the important targets in protein engineering.

For example, it is reported that substitution of a specific amino acid residue in subtilisin BPN' leads to alteration in the pH-dependence by altering the surface charge of the enzyme (Non-patent Documents 2 to 4), M-protease which is a high-alkali resistant protease adapts to high-alkali conditions when the surface amino acid residues are altered to acquire a high isoelectric point and gain a new network of ion bonds (Non-patent Document 5), and that there is a constant relationship between the isoelectric point and the detergency of subtilisin (Patent Document 2).

However, any of the above mentioned reports relates to serine proteases derived from bacteria belonging to *Bacillus* sp., having a molecular weight of approximately 28,000 such as subtilisin BPN' and subtilisin 309. Therefore, the reports do not provide useful information for a group of serine proteases having a gap region and an extended region of the C-terminus, which do not exist in the group of proteases having a molecular weight of approximately 28,000, and having a molecular weight of approximately 43,000.

Moreover, it is impossible to predict whether an alteration of amino acid residues in order to improve detergency of an enzyme will anyhow affect protein productivity or not. Therefore, even though the introduction of a certain mutation can bring a favorable change on detergency, the actual production may be extremely inhibited if it lowers its protein productivity.

[Patent Document 1] WO99/18218
[Patent Document 2] Japanese Patent No. 3343115
[Non-patent Document 1] Saeki et al., Biochem. Biophys. Res. Commun., Vol. 279, pp. 313-319, 2000
[Non-patent Document 2] Nature, Vol. 318, pp. 375-376, 1985
[Non-patent Document 3] J. Mol. Biol., Vol. 193, pp. 803-813, 1987
[Non-patent Document 4] Nature, Vol. 328, pp. 496-500, 1987
[Non-patent Document 5] Protein Engineering, Vol. 10, pp. 627-634, 1997

SUMMARY OF THE INVENTION

The present invention relates to the following inventions:

(1) An alkaline protease, wherein the amino acid residues at (a) position 9, (b) position 49, (c) position 194, (d) position 212, (e) position 237, (f) position 245, (g) position 281, (h) position 313, (i) position 379 and (j) position 427 in SEQ ID NO: 2 are selected from the following amino acid residues;
Position (a); glutamine,
Position (b); glutamine,
Position (c); lysine or arginine,
Position (d); arginine, asparagine or glutamine,
Position (e); asparagine,
Position (f); asparagine,
Position (g); arginine,
Position (h); asparagine,
Position (i); lysine, arginine, glutamic acid or aspartic acid,
Position (j); arginine.

(2) An alkaline protease consisting of an amino acid sequence that has 80% or more homology with the amino acid sequence represented by SEQ ID NO: 2, wherein the amino acid residues corresponding to (a) position 9, (b) position 49, (c) position 194, (d) position 212, (e) position 237, (g) position 281 and (i) position 379 in SEQ ID NO: 2 are selected from the following amino acid residues;
Position (a); glutamine
Position (b); glutamine
Position (c); lysine or arginine
Position (d); asparagine or glutamine
Position (e); asparagine Position (g); arginine Position (i); glutamic acid or aspartic acid.

(3) A gene encoding one of the above mentioned alkaline proteases;

(4) A recombination vector containing the above mentioned gene and a transformant containing the aforementioned vector;

(5) A detergent composition containing one of the above mentioned alkaline proteases.

DISCLOSURE OF THE INVENTION

The present invention relates to the provision of alkaline proteases endowed with industrially sufficient protein productivity and a significant detergency.

The present inventors have conducted various examinations on performance improvement for the group of alkaline proteases having a molecular weight of approximately 43,000. As a result, the present inventors have found that the existence of specific amino acid residues at the specific sites of the amino acid sequence which is exposed to the surface of an enzymatic protein can either maintain or improve its industrially sufficient protein productivity and, moreover, can improve its detergency. Based on these findings, the present inventors have completed the present invention.

According to the present invention, there are provided alkaline proteases which can be produced industrially favorably and have a significant detergency.

The alkaline protease consisting of the amino acid sequence represented by SEQ ID NO: 2 of the present invention represents Protease KP43 [derived from *Bacillus* sp. KSM-KP43 (FERN BP-6532), WO99/18218, GenBank accession no. AB051423]. The amino acid residues at (a) position 9, (b) position 49, (c) position 194, (d) position 212, (e) position 237, (f) position 245, (g) position 281, (h) position 313, (i) position 379 and (j) position 427 of SEQ ID NO: 2 of the alkaline protease of the present invention are selected from the following amino acid residues;

Position (a); glutamine,
Position (b); glutamine,
Position (c); lysine or arginine,
Position (d); arginine, asparagine or glutamine,
Position (e); asparagine,
Position (f); asparagine,
Position (g); arginine,
Position (h); asparagine,
Position (i); lysine, arginine, glutamic acid or aspartic acid,
Position (j); arginine.

The alkaline protease of the present invention may include wild-type, wild-type variants or artificial variants.

Moreover, the alkaline proteases of the present invention include alkaline proteases consisting of an amino acid sequence that has 80% or more homology with the amino acid sequence represented by SEQ ID NO: 2, wherein the amino acid residues corresponding to (a) position 9, (b) position 49, (c) position 194, (d) position 212, (e) position 237, (g) position 281 and (i) position 379 in SEQ ID NO: 2 are selected from the following amino acid residues;

Position (a); glutamine,
Position (b); glutamine,
Position (c); lysine or arginine,
Position (d); asparagine or glutamine,
Position (e); asparagine,
Position (g); arginine,
Position (i); glutamic acid or asparagine acid, and may include wild-type, wild-type variants or artificial variants.

Examples of the alkaline proteases consisting of an amino acid sequence that has 800 or more homology with the amino acid sequence represented by SEQ ID NO: 2 include alkaline proteases consisting of an amino acid sequence that has 95% or more homology with the amino acid sequence represented by SEQ ID NO: 2, preferably 96% or more therewith, more preferably 90% or more therewith, even more preferably 97% or more therewith, more preferably 98% or more therewith, even more preferably 99% or more therewith, all of which have the same level of functions as that of the amino acid sequence represented by SEQ ID NO:2, and alkaline proteases different from alkaline proteases consisting of the amino acid sequence represented by SEQ ID NO: 2 (which may be referred to as "another alkaline protease").

Such another alkaline protease preferably has the properties described in the following (1) or (2).

(1) Having oxidant resistance and a molecular weight of 43,000±2,000 as determined by a sodium dodecyl sulfate polyacrylamide gel electrophoresis (SDS-PAGE) technique.

(2) Functioning in the alkaline region above pH 8, having oxidant resistance, retaining 80% or more residual activity when treated at 50° C. in pH 10 for 10 minutes, being inhibited by diisopropyl fluorophosphates (DFP) and phenylmethanesulfonyl fluoride (PMSF), and having a molecular weight of 43,000±2,000 as determined by SDS-PAGE.

The term "having oxidant resistance" as used herein means to have 50% or more residual activity after being left to stand in a 20 mM Britton Robinson buffer containing 50 mM hydrogen peroxide and 5 mM calcium chloride (pH 10) at 30° C. for 20 minutes.

Examples of aforementioned another alkaline protease include Protease KP9860 [derived from *Bacillus* sp. KSM-KP9860 (FERM BP-6534), WO99/18218, GenBank accession no. AB046403]; Protease E-1 [derived from *Bacillus* No. D-6 (FERM P-1592), Japanese Patent Laid-Open No. 49-71191, GenBank accession no. AB046402]; Protease Ya [derived from *Bacillus* sp. Y (FERM BP-1029), Japanese Patent Laid-Open No. 61-280268, GenBank accession no. AB046404]; Protease SD521 [derived from *Bacillus* SD521 (FERM P-11162), Japanese Patent Laid-Open No. 3-191781, GenBank accession no. AB046405]; Protease A-1 [derived from NCIB12289, WO88/01293, GenBank accession no. AB046406]; Protease A-2 [derived from NCIB12513, WO98/56927]; Protease 9865 [derived from *Bacillus* sp. KSM-9865 (FERM P-18566), GenBank accession no. AB084155] and the variant proteases as described in JP-A-2002-218989, JP-A-2002-306176, JP-A-2003-125783, JP-A-2004-000122, JP-A-2004-057195, JP-A-2004-305175, JP-A-2004-305176, JP-A-2006-129865.

In addition, homologies between different amino acid sequences are calculated by the Lipman-Pearson method (Science, Vol. 227, pp. 1435, (1985)). More specifically, analysis is performed through the use of a homology analysis (Search homology) program developed by the genetic information processing software, Genetyx-Win (Software Development Co., Ltd.), with the parameter Unit size to compare (ktup) being set 2.

Moreover, with the alkaline proteases consisting of an amino acid sequence that has 80% or more homology with the amino acid sequence represented by SEQ ID NO: 2 mentioned above, the amino acid residue corresponding to each of the positions (a), (b), (c), (d), (e), (g) and (i) of SEQ ID NO: 2 can be identified by comparing amino acid sequences between the amino acid sequence represented by SEQ ID NO: 2 and the amino acid sequence of another alkaline protease by means of a publicly known algorithm such as the above mentioned Lipman-Pearson's method, and by maximizing the homology in conserved amino acid residues which are present in the amino acid sequence of each alkaline protease. The positions of corresponding amino acid residues in the sequence of each protease can be determined by aligning the amino acid sequence of the protease through the use of such method, regardless of insertions and deletions within an amino acid sequence. It is presumed that the corresponding positions exist at the three-dimensionally same position, and the amino acid residues existing at the same position bring about similar effects for a specific function of the target protease.

More specifically, an amino acid residue at position of 194 of SEQ ID NO: 2 is a serine residue. The amino acid residue at the position corresponding thereto can be identified as the serine residue at position of 193 in Protease E-1, the serine residue at position of 194 in Protease KP9860, and the serine residue at position of 193 in Protease Ya through alignment of amino acid sequences by employing the method mentioned above.

With regards to another alkaline protease which is preferred among the above mentioned ones, specific examples of a position and an amino acid residue corresponding to the amino acid residues at (a) position 9, (b) position 49, (c) position 194, (d) position 212, (e) position 237, (g) position 281 and (i) position 379 of the amino acid sequence of Protease PK43 (SEQ ID NO: 2) are shown in Table 1.

TABLE 1

| POSITION | KP43 | KP9860 | 9865 | E-1 | Ya | SD-521 | A-1 | A-2 |
|---|---|---|---|---|---|---|---|---|
| (a) | Lys9 | Lys9 | Lys9 | Lys9 | Lys9 | Lys9 | Lys9 | Lys9 |
| (b) | Lys49 | Lys49 | Lys49 | Lys49 | Lys49 | Lys49 | Lys49 | Lys49 |
| (c) | Ser194 | Ser194 | Ser194 | Ser193 | Ser193 | Ser193 | Ser194 | Ser193 |
| (d) | Lys212 | Lys212 | Lys212 | Arg211 | Arg211 | Arg211 | Lys212 | Arg211 |
| (e) | Asp237 | Asp237 | Asp237 | Asp236 | Asp236 | Asp236 | Asp237 | Asp236 |
| (g) | Lys281 | Lys281 | Lys281 | Lys280 | Lys280 | Lys280 | Lys281 | Lys280 |
| (i) | Gln379 | Arg379 | Gln379 | Lys378 | Lys378 | Lys378 | Lys379 | Lys378 |

Furthermore, selection of amino acid residues at positions (a) through (j) and the like in an alkaline protease of the present invention may include substitutions conducted at 2 or more positions selected from positions (a) through (j) and the like simultaneously as long as enzymatic properties are not altered.

When an alkaline protease of the present invention is a variant, an alkaline protease prior to mutation (which may be referred to as a "parent alkaline protease") corresponds to either "a protease consisting of the amino acid sequence represented by SEQ ID NO: 2" or "an alkaline protease consisting of an amino acid sequence that has 80% or more homology with the amino acid sequence represented by SEQ ID NO: 2." By introducing a mutation to a desired site of this protease, the alkaline protease of the present invention can be obtained. For example, the amino acid residues at positions selected from the aforementioned positions (a) through (j) in the amino acid sequence of Protease KP43 represented by SEQ ID NO: 2 or the amino acid residues at positions selected from the aforementioned positions (a), (b), (c), (d), (e), (g) and (i) in the amino acid sequence of an alkaline protease consisting of an amino acid sequence that has 80% or more homology with the amino acid sequence represented by SEQ ID NO: 2 are substituted with other amino acid residues to give the alkaline protease of the present invention.

The alkaline protease of the present invention can be obtained, for example, by the following method. More specifically, a mutation is introduced to a cloned gene encoding a parent alkaline protease (SEQ ID NO: 1) and the resulting variant gene is used to transform a proper host. The aforementioned recombinant host is then cultured, and an alkaline protease is collected from the culture. Cloning of the gene encoding a parent alkaline protease can be performed by an ordinary gene recombination technique, for example, in accordance with the methods as described in WO99/18218 and WO98/56927.

For introducing a mutation to the gene encoding a parent alkaline protease, any of the conventionally used site-specific mutagenesis methods can be employed. More specifically, for example, a Site-Directed Mutagenesis System Mutan-Super Express Km kit (Takara Bio Inc.) can be used. Moreover, by using the recombinant PCR (polymerase chain reaction) method (PCR protocols, Academic Press, New York, 1990), a desired sequence of a gene can be substituted with a sequence of another gene corresponding to the aforementioned desired sequence.

The method for producing the protease of the present invention by using the obtained variant gene includes, for example, ligating the aforementioned variant gene with a DNA vector stably amplifiable followed by transformation of a host bacterium with the vector, or integrating the aforementioned variant gene to a chromosomal DNA in a host bacterium capable of maintaining it stably. These are examples of methods which can be employed. Hosts which satisfy these conditions include, for example, bacteria belonging to *Bacillus* sp., *Escherichia coli*, fungi, yeast, and actinomycetes. These bacterial strains can be inoculated into a medium containing assimilatable carbon sources, nitrogen sources and other essential nutrition to be cultured according to the method known per se.

Collection and purification of an alkaline protease from the obtained culture can be performed in accordance with conventional methods applicable to the collection and purification of common enzymes. For example, the target enzyme can be obtained from culture supernatant by using a conventional purification method after removing bacterial cells by centrifugation or filtration of the culture. The enzyme solution obtained with such method can be used either without further processing or by being further subjected to purification, crystallization, powderization or granulation by known methods.

The alkaline proteases of the present invention thus available have oxidant resistance, are free from the inhibition of caseinolytic activity by a high concentration of a fatty acid, have a molecular weight of 43,000±2,000 as determined by SDS-PAGE, are active in the alkaline region, exert improved detergency, and show industrially sufficient productivity. Namely, in the case of naturally occurring enzymes, the enzymes have newly acquired properties of maintaining 90% or more protein productivity of Protease KP43 represented by SEQ ID NO: 2, and preferably maintaining 95% or more therewith or exceeding the protein productivity of Protease KP43. In addition, in the case of variants, the enzymes have newly acquired properties of maintaining 90% or more protein productivity of a parent enzyme thereof, preferably maintaining 95% or more therewith, and more preferably obtaining protein productivity greater than or equivalent to that of a parent alkaline protease.

Therefore, the alkaline protease of the present invention is effective as an enzyme to be incorporated in various detergent compositions.

The protease of the present invention may be incorporated to the detergent composition in an amount sufficient to permit exhibition of its activity without limitation. Although it can be incorporated in an amount from 0.1 to 5000 PU per kg of the detergent composition, preferably 500 PU or less is incorporated in consideration of economy and the like.

To the detergent composition of the present invention, various enzymes can be used in combination with the protease of the present invention. Examples include hydrolases, oxidases, reductases, transferases, lyases, isomerases, ligases and synthetases. Of these, proteases other than the alkaline protease used in the present invention, cellulases, keratinases, esterases, cutinases, amylases, lipases, pullulanases, pectinases, mannases, glucosidases, glucanases, cholesterol oxidases, peroxidases, laccases and the like are preferred. Proteases, cellulases, amylases and lipases are particularly preferred. Examples of proteases include commercially available Alcalase, Esperase, Savinase, Everlase and Kannase (registered trademarks; Novozymes A/S), Properase and Purafect (trademarks; Genencor International Inc.), and KAP (registered trademark; Kao Corporation). Cellulases include Cellzyme and Carezyme (registered trademarks; Novozymes A/S), KAC, the alkaline cellulase produced by *Bacillus* sp. strain KSM-S237 as described in Japanese Patent No. 10-313859 and the variant alkaline cellulase as described in Japanese Patent Application No. 2002-116553 (each, registered trademark; Kao Corporation) and the like. Amylases include Termamyl and Duramyl (registered trademarks; Novozymes A/S), Purastar (registered trademarks; Genencor International Inc.), and KAM (registered trademark; Kao Corporation) and the like. Lipases include Lipolase and Lipolase Ultra (registered trademarks; Novozymes A/S).

When a protease other than the protease used in the present invention is used in combination for a detergent composition, preferably the protease is incorporated in an amount from 0.1 to 500 PU per kg of the detergent composition. When cellulase is used in combination, preferably the cellulase is incorporated in an amount from 300 to 3000000 KU per kg of the detergent composition based on the unit (KU) determined by the method of measuring enzymatic activity as described in Paragraph [0020] in Japanese Patent No. 10-313859.

When amylase is used in combination, preferably the amylase is incorporated in an amount from 50 to 500000 IU per kg of the detergent composition based on the unit (IU) determined by the method of measuring amylase activity as described in Paragraph [0040] in Japanese Patent No. 11-43690.

Moreover, when lipase is used in combination, preferably the lipase is incorporated in an amount from 10000 to 1000000 LU per kg of the detergent composition based on the unit (LU) determined by the method of measuring lipase activity as described in Example 1 in Japanese Patent No. 8-500013.

To the detergent composition of the present invention, publicly known detergent components can be incorporated. Examples of the aforementioned publicly known detergent components include the following.

(1) Surfactant

A surfactant may be incorporated in an amount of 0.5 to 60% by weight in the detergent composition. In particular, to a powdery detergent composition and a liquid detergent composition, addition of 10 to 45% by weight and 20 to 50% by weight are preferred, respectively. When the detergent composition of the present invention is a bleaching agent or automatic dishwasher detergent, the surfactant may generally be incorporated in an amount of 1 to 10% by weight, and preferably 1 to 5% by weight.

Examples of surfactant to be used in the detergent composition of the present invention include an anionic surfactant, non-ionic surfactant, ampholytic surfactant and cationic surfactant or combinations thereof. An anionic surfactant and non-ionic surfactant are preferred.

Examples of anionic surfactant include the salts of alcohol sulfates having 10 to 18 carbon atoms, the salts of alcohol alkoxylate sulfates, alkyl benzene sulfonates, paraffin sulfonates, α-olefin sulfonates, α-sulfo fatty acids, α-sulfo fatty acid alkylesters or fatty acid salts having 8 to 20 carbon atoms. Particularly preferred in the present invention are linear alkyl benzene sulfonates with an alkyl chain having 10 to 14 carbon atoms, and more preferably 12 to 14 carbon atoms. As a counter ion, alkali metal salts and amines are preferred. Particularly preferred are sodium and/or potassium, monoethanolamine and diethanolamine.

Preferred examples of non-ionic surfactant include polyoxyalkylenealkyl (with 8 to 20 carbon atoms) ether, alkyl polyglucoside, polyoxyalkylenealkyl (with 8 to 20 carbon atoms) phenyl ether, polyoxyalkylene sorbitan fatty acid (with 8 to 22 carbon atoms) ester, polyoxyalkylene glycol fatty acid (with 8 to 22 carbon atoms) ester, polyoxyethylenepolyoxypropylene block polymer. Particularly preferred nonionic surfactant is a polyoxyalkylenealkyl ether [with a HLB value, as calculated by the Griffin method, in the range of 10.5 to 15.0, and more preferably 11.0 to 14.5], wherein alkyleneoxide such as ethyleneoxide and propyleneoxide is added in an amount of 4 to 20 mol to alcohol having 10 to 18 carbon atoms.

(2) Divalent Metal Ion Scavenger

A divalent metal ion scavenger may be incorporated in an amount of 0.01 to 50% by weight, and preferably 5 to 40% by weight. Examples of divalent metal ion scavenger to be used in the detergent composition of the present invention include condensed phosphates such as tripolyphosphate, pyrophosphate and orthophosphate, aluminosilicates such as zeolite, synthetic laminated crystalline silicates, nitrilotriacetic acid salts, ethylenediaminetetraacetic acids, citrates, isocitrates, polyacetalcarboxylates. Of these, crystalline aluminosilicates (synthetic zeolites) are particularly preferred. Among A-type, X-type and P-type zeolites, A-type ones are particularly preferred. As a synthetic zeolite, one with an average primary particle diameter ranging from 0.1 to 10 μm is preferred, and one with an average primary particle diameter ranging from 0.1 to 5 μm is particularly preferred.

(3) Alkaline Agent

An alkaline agent may be incorporated in an amount of 0.01 to 80% by weight, and preferably 1 to 40% by weight. Examples of alkaline agent to be used for a powdery detergent include alkali metal carbonates such as sodium carbonate collectively known as dense soda ash and light soda ash, as well as amorphous alkaline metal silicates such as JIS No. 1, No. 2 and No. 3. These inorganic alkaline agents are effective in skeletal formation of particles during drying a detergent, and thus can provide a relatively hard and significantly fluid detergent. Examples of alkaline agents other than these include sodium sesquicarbonate and sodium hydrogen carbonate. In addition, phosphates such as tripolyphosphate also have the activity of an alkaline agent. Examples of alkaline agent to be used for a liquid detergent include the above mentioned alkaline agents, sodium hydroxide, monoethanolamine, diethanolamine or triethanolamine. These can be used as a counter ion for the activator.

(4) Recontamination Inhibitor

A recontamination inhibitor may be incorporated in an amount of 0.001 to 10% by weight, and preferably 1 to 5% by weight. Examples of recontamination inhibitor to be used in the detergent composition of the present invention include polyethyleneglycol, carboxylic acid-type polymers, polyvinyl alcohol and polyvinylpyrrolidone. Of these, carboxylic acid-type polymers have an ability to inhibit re-contamination, an ability to capture metal ions, an effect to disperse solid particle stains from clothes into a laundry bath. Carboxylic acid-type polymers are either homopolymers or copolymers of acrylic acid, methacrylic acid, itaconic acid and the like. For a copolymer, preferred is a monomer mentioned above copolymerized with maleic acid, having a several thousand to a hundred thousand molecular weight. Apart from the above mentioned carboxylic acid-type polymers, polymers of the salts of polyglycidyl acid and the like, cellulose derivatives such as carboxymethyl cellulose, and aminocarboxylic acid-type polymers such as polyaspartic acid are preferred because they also have the ability to serve as metal ion scavengers, dispersants, and possess an ability to inhibit re-contamination.

(5) Bleaching Agent

A bleaching agent such as hydrogen peroxide and percarbonate is incorporated preferably in an amount of 1 to 10% by weight. When the bleaching agent is used, 0.01 to 10% by weight of a bleaching activator (activator) such as tetraacetylethylenediamine (TAED) and the bleaching activator as described in Japanese Patent No. 6-316700 can be added.

(6) Fluorescent Brightener

As a fluorescent brightener to be used in the detergent composition of the present invention, biphenyl type fluorescent brighteners (such as Tinopal CBS-X) and stilbene type fluorescent brighteners (such as DM type fluorescent dye) can be used. A fluorescent brightener is incorporated preferably in an amount of 0.001 to 2% by weight.

(7) Other Component

To the detergent composition of the present invention, builders, tenderizers, reducing agents (such as sulfite), foaming inhibitors (such as silicone), fragrances and other additives, which are known to those skilled in the art of laundry detergent, may be included.

The detergent composition of the present invention can be manufactured in accordance with the law of the art by using the protease of the present invention obtained by the above mentioned method and the above mentioned publicly known detergent components in combination. The detergent form can be selected according to the using purpose. Examples include liquid, powder, granule, paste and solid.

The detergent composition of the present invention thus available is usable as a laundry detergent, bleaching agent, hard surface cleaning detergent, pipe cleaner, artificial tooth cleaner, antimicrobial cleaner for medical apparatus and the like.

EXAMPLES

The present invention will now be described in connection with certain examples more specifically hereinafter.

Example 1

For a region of approximately 2.0 kb including up to the stop codon of an alkaline protease structural gene derived from *Bacillus* sp. KSM-KP43 (SEQ ID NO: 1), primers were designed to introduce site-specific mutations at (1) position 9, (2) position 49, (3) position 194, (4) position 212, (5) position 237, (6) position 245, (7) position 281, (8) position 313, (9) position 379 and (10) position 427 of the mature enzyme region.

PCR was conducted by use of the following primers, respectively.

(1) Primer 1 (SEQ ID NO: 3) and Primer 3 (SEQ ID NO: 5) as well as Primer 4 (SEQ ID NO: 6) and Primer 2 (SEQ ID NO: 4) to introduce a glutamine at position 9;

(2) Primer 1 (SEQ ID NO: 3) and Primer 5 (SEQ ID NO: 7) as well as Primer 6 (SEQ ID NO: 8) and Primer 2 (SEQ ID NO: 4) to introduce a glutamine at position 49;

(3) Primer 1 (SEQ ID NO: 3) and Primer 7 (SEQ ID NO: 9) as well as Primer 8 (SEQ ID NO: 10) and Primer 2 (SEQ ID NO: 4) to introduce a lysine at position 194; Primer 1 (SEQ ID NO: 3) and Primer 7 (SEQ ID NO: 9) as well as Primer 9 (SEQ ID NO: 11) and Primer 2 (SEQ ID NO: 4) to introduce an arginine at position 194;

(4) Primer 1 (SEQ ID NO: 3) and Primer 10 (SEQ ID NO: 12) as well as Primer 11 (SEQ ID NO: 13) and Primer 2 (SEQ ID NO: 4) to introduce an arginine at position 212; Primer 1 (SEQ ID NO: 3) and Primer 10 (SEQ ID NO: 12) as well as Primer 12 (SEQ ID NO: 14) and Primer 2 (SEQ ID NO: 4) to introduce an asparagine at position 212; Primer 1 (SEQ ID NO: 3) and Primer 10 (SEQ ID NO: 12) as well as Primer 13 (SEQ ID NO: 15) and Primer 2 (SEQ ID NO: 4) to introduce a glutamine at position 212;

(5) Primer 1 (SEQ ID NO: 3) and Primer 14 (SEQ ID NO: 16) as well as Primer 15 (SEQ ID NO: 17) and Primer 2 (SEQ ID NO: 4) to introduce an asparagine at position 237;

(6) Primer 1 (SEQ ID NO: 3) and Primer 14 (SEQ ID NO: 16) as well as Primer 16 (SEQ ID NO: 18) and Primer 2 (SEQ ID NO: 4) to introduce an asparagine at position 245;

(7) Primer 1 (SEQ ID NO: 3) and Primer 17 (SEQ ID NO: 19) as well as Primer 18 (SEQ ID NO: 20) and Primer 2 (SEQ ID NO: 4) to introduce an arginine at position 281;

(8) Primer 1 (SEQ ID NO: 3) and Primer 19 (SEQ ID NO: 21) as well as Primer 20 (SEQ ID NO: 22) and Primer 2 (SEQ ID NO: 4) to introduce an asparagine at position 313;

(9) Primer 1 (SEQ ID NO: 3) and Primer 21 (SEQ ID NO: 23) as well as Primer 22 (SEQ ID NO: 24) and Primer 2 (SEQ ID NO: 4) to introduce a lysine at position 379; Primer 1 (SEQ ID NO: 3) and Primer 21 (SEQ ID NO: 23) as well as Primer 23 (SEQ ID NO: 25) and Primer 2 (SEQ ID NO: 4) to introduce an arginine at position 379; Primer 1 (SEQ ID NO: 3) and Primer 21 (SEQ ID NO: 23) as well as Primer 24 (SEQ ID NO: 26) and Primer 2 (SEQ ID NO: 4) to introduce an aspartic acid at position 379; Primer 1 (SEQ ID NO: 3) and Primer 21 (SEQ ID NO: 23) as well as Primer 25 (SEQ ID NO: 27) and Primer 2 (SEQ ID NO: 4) to introduce a glutaminic acid at position 379; and

(10) Primer 1 (SEQ ID NO: 3) and Primer 26 (SEQ ID NO: 28) as well as Primer 27 (SEQ ID NO: 29) and Primer 2 (SEQ ID NO: 4) to introduce an arginine at position 427.

A BamHI linker was added to the 5' end of the sense strand of Primer 1, and an XbaI linker was added to the 5' end of the antisense strand of Primer 2. Primer 3 and Primer 4, Primer 5 and Primer 6, Primer 7 and Primer 8, Primer 7 and Primer 9, Primer 10 and Primer 11, Primer 10 and Primer 12, Primer 10 and Primer 13, Primer 14 and Primer 15, Primer 14 and Primer 16, Primer 17 and Primer 18, Primer 19 and Primer 20, Primer 21 and Primer 22, Primer 21 and Primer 23, Primer 21 and Primer 24, Primer 21 and Primer 25, and Primer 26 and Primer 27 were designed to have a 10 to 15-bp sequence mutually complementary at the 5' end, respectively. In PCR, the template DNA was denatured at 94° C. for 2 minutes, followed by 30 cycles of treatment, each cycle of 94° C. for 1 minute, 55° C. for 1 minute, and 72° C. for 1 minute, using Pyrobest (Takara Bio Inc.) as a DNA polymerase. The amplified DNA fragments were purified by use of PCR product purification kit (Roche Ltd.). Subsequently, recombinant PCR was performed, wherein the denaturation was carried out at 94° C. for 2 minutes, followed by 30 cycles of treatment, each cycle of 94° C. for 1 minute, 55° C. for 1 minute, and 72° C. for 1 minute, only with the amplified fragments corresponding thereto, respectively. For the obtained amplified fragments, PCR was performed using Primer 1 and Primer 4. In PCR, the template DNA was denatured at 94° C. for 2 minutes, followed by 30 cycles of treatment, each cycle of 94° C. for 1 minute, 55° C. for 1 minute, and 72° C. for 2 minute. As a result, the full-length gene with a mutation introduced was obtained. After purifying the amplified fragments, the restriction enzyme linkers added to the ends were cleaved with BamHI and XbaI (Roche Ltd.). The amplified DNA fragments were mixed with plasmid pHA64 which had undergone treatment with BamHI and XbaI (Japanese Patent No. 349293, BamHI- and XbaI-cleaved sites are contained in a downstream region of promoter 64) and subsequently, ligation reaction was carried out with Ligation High (Toyobo Co., Ltd.). Through ethanol precipitation, plasmid was recovered from the reaction mixture and *Bacillus* sp. KSM-9865 strain (FERM P-18566) serving as the host bacterium was transformed therewith.

The 9865 strain transformants were grown on a skim milk-containing alkaline agar medium [skim milk (Difco Laboratories) 1% (w/v), bactotryptone (Difco Laboratories) 1%, yeast extract (Difco Laboratories) 0.5%, sodium chloride 1%, agar 1.5%, sodium carbonate 0.05%, and tetracycline 15 ppm]. Whether or not a mutated protease gene had been introduced was determined on the basis of halo formation. The transformants were inoculated into 5 ml of a seed culture medium [6.0% (w/v) polypeptone S, 0.05% of yeast extract, 1.0% of maltose, 0.02% of magnesium sulfate heptahydrate, 0.1% of potassium dihydrogenphosphate, 0.25% of sodium carbonate, and 30 ppm of tetracycline], followed by shaking the culture for 16 hours at 30° C. The seed culture broth (1% (v/v)) was subsequently inoculated into 30 ml of a main culture medium [8% polypeptone S, 0.3% of yeast extract, 10% of maltose, 0.04% of magnesium sulfate heptahydrate, 0.2% of potassium dihydrogenphosphate, 1.5% of sodium carbonate anhydrate, and 30 ppm tetracycline], followed by shaking the culture for three days at 30° C.

The obtained culture was subjected to centrifugation, and the protein amount was measured by use of Protein assay kit (Wako Pure Chemical Industries, Ltd.). Through comparison with a measurement obtained from a culture supernatant of a culture, wherein the culturing was performed under the same culture conditions, of a transformant harboring a parent enzyme gene, the productivity of the mutated protease genes was evaluated (Table 2). Table 3 shows the results of detergency evaluation for the obtained enzyme solutions at pH 10 and pH 10.5.

It was confirmed that the above mentioned variant alkaline protease of the present invention had the properties of a parent alkaline protease, apart from improving detergency. More specifically, it had oxidant resistance, was free from the inhibition of caseinolytic activity by a high concentration of a fatty acid, had a molecular weight of 43,000±2,000 as determined by SDS-PAGE, and possessed an activity in the alkaline region.

Method for Measuring Protease Activity (Casein Method)

After 1 ml of 50 mM of a borate buffer solution (pH 10.5) containing 1% (w/v) Casein (Hammerstein method: Merck Inc.) was maintained at 30° C. for 5 minutes, 0.1 ml of an enzyme solution was added to initiate the reaction. After reaction for 15 minutes, 2 ml of a reaction termination solution (0.11 M trichloroacetic acid/0.22 M sodium acetate/0.33 M acetic acid) was added. The mixture was left to stand at room temperature for 30 minutes. Subsequently, the precipitation was filtered by use of Whattmann No. 2 filter paper. The degradation products were quantified by the method according to Lowry et al. More specifically, to 0.5 ml of the filtrate, 2.5 ml of alkaline copper solution (1% Rochelle salt:1% copper sulfate pentahydrate:2% sodium carbonate/0.1 N sodium hydroxide=1:1:100) was added, and after the solution was maintained at 30° C. for 10 minutes, 0.25 ml of phenol reagent (a solution of a commercially available phenol reagent (Kanto Chemical Co., Inc.) diluted two-fold with deionized water) was added and agitated sufficiently. After being left to stand at 30° C. for 30 minutes, the solution was subjected to an absorbance measurement at 660 nm. One unit of protease (1 PU) was defined as the amount of enzyme required for producing acid-soluble protein equivalent to 1 mmol of tyrosine per minute under the above mentioned reaction conditions.

Relative Detergency Ratio

Detergency evaluation for the variant enzymes was performed by use of a Terg-O-Tometer (Ueshima Seisakusho Co., Ltd.). A solution of a commercially available laundry detergent was prepared to reach a desired concentration to be used, and 10% (w/v) sulfuric acid or 10 N sodium hydroxide was added to adjust the pH if desired. An enzyme was added to reach a final concentration of 40 mPU/1. A test cloth EMPA117 (EMPA Testmaterialen, blood/milk/carbon) cut into a piece of 6×6 cm was subsequently added and washed at 20° C. and 80 rpm unless otherwise specified. After rinsing with tap water, the brightness was measured using a colorimeter (Konica Minolta Holdings, Inc., CM3500d). A detergency ratio was calculated based on changes in brightness before and after washing (the following equation).

$$\text{Detergency ratio (\%)}=(L_2-L_1)/(L_0-L_1)\times 100$$

$L_0$: Brightness of the original cloth of the test cloth
$L_1$: Brightness of the test cloth before washing
$L_2$: Brightness of the test cloth after washing Relative detergency ratio was calculated based on the following equation.

$$\text{Relative detergency ratio (\%)}=(\text{Detergency ratio for a variant enzyme–detergency ratio for an enzyme-free detergent solution})/(\text{detergency ratio for a parent enzyme–detergency ratio for an enzyme-free detergent solution})\times 100$$

TABLE 2

| | RELATIVE PROTEIN PRODUCTIVITY (%) |
|---|---|
| K9Q | 95 |
| K49Q | 94 |
| S194K | 110 |
| S194R | 105 |
| K212R | 108 |
| K212N | 98 |
| K212Q | 112 |
| D237N | 95 |
| D245N | 94 |
| K281R | 91 |
| D313N | 103 |
| Q379K | 100 |
| Q379R | 101 |
| Q379E | 97 |
| Q379D | 98 |
| T427R | 101 |
| PARENT ENZYME | 100 |

TABLE 3

| | RELATIVE DETERGENCY (%) | |
|---|---|---|
| | pH 10 | pH 10.5 |
| K9Q | 119 | 83 |
| K49Q | 159 | 95 |
| S194K | 86 | 106 |
| S194R | 72 | 199 |
| K212R | 90 | 123 |
| K212N | 103 | 86 |
| K212Q | 122 | 77 |
| D237N | 99 | 116 |
| D245N | 104 | 107 |
| K281R | 91 | 108 |
| D313N | 90 | 116 |
| Q379K | 78 | 135 |
| Q379R | 75 | 125 |
| Q379E | 111 | 79 |
| Q379D | 123 | 98 |
| T427R | 67 | 124 |
| PARENT ENZYME | 100 | 100 |

SEQUENCE LISTING

<160> NUMBER OF SEQ ID NOS: 29

<210> SEQ ID NO 1
<211> LENGTH: 1923
<212> TYPE: DNA
<213> ORGANISM: Bacillus sp. KSM-KP43
<220> FEATURE:
<221> NAME/KEY: CDS
<222> LOCATION: (1)..(1923)
<220> FEATURE:
<221> NAME/KEY: mat_peptide
<222> LOCATION: (619)..(1920)

<400> SEQUENCE: 1

```
atg aga aag aag aaa aag gtg ttt tta tct gtt tta tca gct gca       45
Met Arg Lys Lys Lys Lys Val Phe Leu Ser Val Leu Ser Ala Ala
    -205              -200              -195 gcg att ttg tcg act gtt gcg tta agt aat cca tct gca ggt ggt       90
Ala Ile Leu Ser Thr Val Ala Leu Ser Asn Pro Ser Ala Gly Gly
    -190              -185              -180 gca agg aat ttt gat ctg gat ttc aaa gga att cag aca aca act      135
Ala Arg Asn Phe Asp Leu Asp Phe Lys Gly Ile Gln Thr Thr Thr
    -175              -170              -165 gat gct aaa ggt ttc tcc aag cag ggg cag act ggt gct gct gct      180
Asp Ala Lys Gly Phe Ser Lys Gln Gly Gln Thr Gly Ala Ala Ala
    -160              -155              -150 ttt ctg gtg gaa tct gaa aat gtg aaa ctc cca aaa ggt ttg cag      225
Phe Leu Val Glu Ser Glu Asn Val Lys Leu Pro Lys Gly Leu Gln
    -145              -140              -135 aag aag ctt gaa aca gtc ccg gca aat aat aaa ctc cat att atc      270
Lys Lys Leu Glu Thr Val Pro Ala Asn Asn Lys Leu His Ile Ile
    -130              -125              -120 caa ttc aat gga cca att tta gaa gaa aca aaa cag cag ctg gaa      315
Gln Phe Asn Gly Pro Ile Leu Glu Glu Thr Lys Gln Gln Leu Glu
    -115              -110              -105 aaa aca ggg gca aag att ctc gac tac ata cct gat tat gct tac att  363
Lys Thr Gly Ala Lys Ile Leu Asp Tyr Ile Pro Asp Tyr Ala Tyr Ile
    -100              -95               -90 gtc gag tat gag ggc gat gtt aag tca gca aca agc acc att gag cac  411
```

-continued

| | | | | | | | | | | | | | |
|---|---|---|---|---|---|---|---|---|---|---|---|---|---|
| Val | Glu | Tyr | Glu | Gly | Asp | Val | Lys | Ser | Ala | Thr | Ser | Thr | Ile | Glu | His |
| -85 | | | | -80 | | | | -75 | | | | -70 | |

```
gtg gaa tcc gtg gag cct tat ttg ccg ata tac aga ata gat ccc cag      459
Val Glu Ser Val Glu Pro Tyr Leu Pro Ile Tyr Arg Ile Asp Pro Gln
                -65                 -60                 -55 ctt ttc aca aaa ggg gca tca gag ctt gta aaa gca gtg gcg ctt gat      507
Leu Phe Thr Lys Gly Ala Ser Glu Leu Val Lys Ala Val Ala Leu Asp
            -50                 -45                 -40 aca aag cag aaa aat aaa gag gtg caa tta aga ggc atc gaa caa atc      555
Thr Lys Gln Lys Asn Lys Glu Val Gln Leu Arg Gly Ile Glu Gln Ile
        -35                 -30                 -25 gca caa ttc gca ata agc aat gat gtg cta tat att acg gca aag cct      603
Ala Gln Phe Ala Ile Ser Asn Asp Val Leu Tyr Ile Thr Ala Lys Pro
    -20                 -15                 -10 gag tat aag gtg atg aat gat gtt gcg cgt gga att gtc aaa gcg gat      651
Glu Tyr Lys Val Met Asn Asp Val Ala Arg Gly Ile Val Lys Ala Asp
-5                   -1  1                  5                  10 gtg gct cag agc agc tac ggg ttg tat gga caa gga cag atc gta gcg      699
Val Ala Gln Ser Ser Tyr Gly Leu Tyr Gly Gln Gly Gln Ile Val Ala
                15                  20                  25 gtt gcc gat aca ggg ctt gat aca ggt cgc aat gac agt tcg atg cat      747
Val Ala Asp Thr Gly Leu Asp Thr Gly Arg Asn Asp Ser Ser Met His
            30                  35                  40 gaa gcc ttc cgc ggg aaa att act gca tta tat gca ttg gga cgg acg      795
Glu Ala Phe Arg Gly Lys Ile Thr Ala Leu Tyr Ala Leu Gly Arg Thr
        45                  50                  55 aat aat gcc aat gat acg aat ggt cat ggt acg cat gtg gct ggc tcc      843
Asn Asn Ala Asn Asp Thr Asn Gly His Gly Thr His Val Ala Gly Ser
60                  65                  70                  75 gta tta gga aac ggc tcc act aat aaa gga atg gcg cct cag gcg aat      891
Val Leu Gly Asn Gly Ser Thr Asn Lys Gly Met Ala Pro Gln Ala Asn
                80                  85                  90 cta gtc ttc caa tct atc atg gat agc ggt ggg gga ctt gga gga cta      939
Leu Val Phe Gln Ser Ile Met Asp Ser Gly Gly Gly Leu Gly Gly Leu
            95                  100                 105 cct tcg aat ctg caa acc tta ttc agc caa gca tac agt gct ggt gcc      987
Pro Ser Asn Leu Gln Thr Leu Phe Ser Gln Ala Tyr Ser Ala Gly Ala
        110                 115                 120 aga att cat aca aac tcc tgg gga gca gca gtg aat ggg gct tac aca     1035
Arg Ile His Thr Asn Ser Trp Gly Ala Ala Val Asn Gly Ala Tyr Thr
    125                 130                 135 aca gat tcc aga aat gtg gat gac tat gtg cgc aaa aat gat atg acg     1083
Thr Asp Ser Arg Asn Val Asp Asp Tyr Val Arg Lys Asn Asp Met Thr
140                 145                 150                 155 atc ctt ttc gct gcc ggg aat gaa gga ccg aac ggc gga acc atc agt     1131
Ile Leu Phe Ala Ala Gly Asn Glu Gly Pro Asn Gly Gly Thr Ile Ser
                160                 165                 170 gca cca ggc aca gct aaa aat gca ata aca gtc gga gct acg gaa aac     1179
Ala Pro Gly Thr Ala Lys Asn Ala Ile Thr Val Gly Ala Thr Glu Asn
            175                 180                 185 ctc cgc cca agc ttt ggg tct tat gcg gac aat atc aac cat gtg gca     1227
Leu Arg Pro Ser Phe Gly Ser Tyr Ala Asp Asn Ile Asn His Val Ala
        190                 195                 200 cag ttc tct tca cgt gga ccg aca aag gat gga cgg atc aaa ccg gat     1275
Gln Phe Ser Ser Arg Gly Pro Thr Lys Asp Gly Arg Ile Lys Pro Asp
    205                 210                 215 gtc atg gca ccg gga acg ttc ata cta tca aga tct tct ctt gca         1323
Val Met Ala Pro Gly Thr Phe Ile Leu Ser Arg Ser Ser Leu Ala
220                 225                 230                 235 ccg gat tcc tcc ttc tgg gcg aac cat gac agt aaa tat gca tac atg     1371
Pro Asp Ser Ser Phe Trp Ala Asn His Asp Ser Lys Tyr Ala Tyr Met
```

```
Pro Asp Ser Ser Phe Trp Ala Asn His Asp Ser Lys Tyr Ala Tyr Met
            240                 245                 250 ggt gga acg tcc atg gct aca ccg atc gtt gct gga aac gtg gca cag      1419
Gly Gly Thr Ser Met Ala Thr Pro Ile Val Ala Gly Asn Val Ala Gln
            255                 260                 265 ctt cgt gag cat ttt gtg aaa aac aga ggc atc aca cca aag cct tct      1467
Leu Arg Glu His Phe Val Lys Asn Arg Gly Ile Thr Pro Lys Pro Ser
            270                 275             280 cta tta aaa gcg gca ctg att gcc ggt gca gct gac atc ggc ctt ggc      1515
Leu Leu Lys Ala Ala Leu Ile Ala Gly Ala Ala Asp Ile Gly Leu Gly
        285                 290                 295 tac ccg aac ggt aac caa gga tgg gga cga gtg aca ttg gat aaa tcc      1563
Tyr Pro Asn Gly Asn Gln Gly Trp Gly Arg Val Thr Leu Asp Lys Ser
300                 305                 310                 315 ctg aac gtt gcc tat gtg aac gag tcc agt tct cta tcc acc agc caa      1611
Leu Asn Val Ala Tyr Val Asn Glu Ser Ser Ser Leu Ser Thr Ser Gln
                320                 325                 330 aaa gcg acg tac tcg ttt act gct act gcc ggc aag cct ttg aaa atc      1659
Lys Ala Thr Tyr Ser Phe Thr Ala Thr Ala Gly Lys Pro Leu Lys Ile
            335                 340                 345 tcc ctg gta tgg tct gat gcc cct gcg agc aca act gct tcc gta acg      1707
Ser Leu Val Trp Ser Asp Ala Pro Ala Ser Thr Thr Ala Ser Val Thr
        350                 355                 360 ctt gtc aat gat ctg gac ctt gtc att acc gct cca aat ggc aca cag      1755
Leu Val Asn Asp Leu Asp Leu Val Ile Thr Ala Pro Asn Gly Thr Gln
    365                 370                 375 tat gta gga aat gac ttt act tcg cca tac aat gat aac tgg gat ggc      1803
Tyr Val Gly Asn Asp Phe Thr Ser Pro Tyr Asn Asp Asn Trp Asp Gly
380                 385                 390                 395 cgc aat aac gta gaa aat gta ttt att aat gca cca caa agc ggg acg      1851
Arg Asn Asn Val Glu Asn Val Phe Ile Asn Ala Pro Gln Ser Gly Thr
                400                 405                 410 tat aca att gag gta cag gct tat aac gta ccg gtt gga cca cag acc      1899
Tyr Thr Ile Glu Val Gln Ala Tyr Asn Val Pro Val Gly Pro Gln Thr
            415                 420                 425 ttc tcg ttg gca att gtg aat taa                                      1923
Phe Ser Leu Ala Ile Val Asn
        430

<210> SEQ ID NO 2
<211> LENGTH: 640
<212> TYPE: PRT
<213> ORGANISM: Bacillus sp. KSM-KP43

<400> SEQUENCE: 2

Met Arg Lys Lys Lys Lys Val Phe Leu Ser Val Leu Ser Ala Ala
    -205                -200                -195

Ala Ile Leu Ser Thr Val Ala  Leu Ser Asn Pro  Ser Ala Gly Gly
        -190                -185                -180

Ala Arg Asn Phe Asp Leu Asp  Phe Lys Gly Ile Gln  Thr Thr Thr
    -175                -170                -165

Asp Ala Lys Gly Phe Ser Lys  Gln Gly Gln Thr Gly  Ala Ala Ala
    -160                -155                -150

Phe Leu Val Glu Ser Glu Asn  Val Lys Leu Pro Lys  Gly Leu Gln
    -145                -140                -135

Lys Lys Leu Glu Thr Val Pro  Ala Asn Asn Lys Leu  His Ile Ile
    -130                -125                -120

Gln Phe Asn Gly Pro Ile Leu  Glu Glu Thr Lys Gln  Gln Leu Glu
    -115                -110                -105
```

-continued

```
Lys Thr Gly Ala Lys Ile Leu Asp Tyr Ile Pro Asp Tyr Ala Tyr Ile
    -100              -95                  -90

Val Glu Tyr Glu Gly Asp Val Lys Ser Ala Thr Ser Thr Ile Glu His
-85              -80                  -75              -70

Val Glu Ser Val Glu Pro Tyr Leu Pro Ile Tyr Arg Ile Asp Pro Gln
                -65                  -60                  -55

Leu Phe Thr Lys Gly Ala Ser Glu Leu Val Lys Ala Val Ala Leu Asp
                -50                  -45              -40

Thr Lys Gln Lys Asn Lys Glu Val Gln Leu Arg Gly Ile Glu Gln Ile
        -35              -30                  -25

Ala Gln Phe Ala Ile Ser Asn Asp Val Leu Tyr Ile Thr Ala Lys Pro
    -20              -15                  -10

Glu Tyr Lys Val Met Asn Asp Val Ala Arg Gly Ile Val Lys Ala Asp
-5              -1   1                   5                   10

Val Ala Gln Ser Ser Tyr Gly Leu Tyr Gly Gln Gly Gln Ile Val Ala
                15                  20                  25

Val Ala Asp Thr Gly Leu Asp Thr Gly Arg Asn Asp Ser Ser Met His
            30                  35                  40

Glu Ala Phe Arg Gly Lys Ile Thr Ala Leu Tyr Ala Leu Gly Arg Thr
45                  50                  55

Asn Asn Ala Asn Asp Thr Asn Gly His Gly Thr His Val Ala Gly Ser
60                  65                  70                  75

Val Leu Gly Asn Gly Ser Thr Asn Lys Gly Met Ala Pro Gln Ala Asn
                80                  85                  90

Leu Val Phe Gln Ser Ile Met Asp Ser Gly Gly Leu Gly Gly Leu
                95                  100                 105

Pro Ser Asn Leu Gln Thr Leu Phe Ser Gln Ala Tyr Ser Ala Gly Ala
                110                 115                 120

Arg Ile His Thr Asn Ser Trp Gly Ala Ala Val Asn Gly Ala Tyr Thr
    125                 130                 135

Thr Asp Ser Arg Asn Val Asp Asp Tyr Val Arg Lys Asn Asp Met Thr
140                 145                 150                 155

Ile Leu Phe Ala Ala Gly Asn Glu Gly Pro Asn Gly Gly Thr Ile Ser
                160                 165                 170

Ala Pro Gly Thr Ala Lys Asn Ala Ile Thr Val Gly Ala Thr Glu Asn
                175                 180                 185

Leu Arg Pro Ser Phe Gly Ser Tyr Ala Asp Asn Ile Asn His Val Ala
                190                 195                 200

Gln Phe Ser Ser Arg Gly Pro Thr Lys Asp Gly Arg Ile Lys Pro Asp
    205                 210                 215

Val Met Ala Pro Gly Thr Phe Ile Leu Ser Ala Arg Ser Ser Leu Ala
220                 225                 230                 235

Pro Asp Ser Ser Phe Trp Ala Asn His Asp Ser Lys Tyr Ala Tyr Met
                240                 245                 250

Gly Gly Thr Ser Met Ala Thr Pro Ile Val Ala Gly Asn Val Ala Gln
                255                 260                 265

Leu Arg Glu His Phe Val Lys Asn Arg Gly Ile Thr Pro Lys Pro Ser
    270                 275                 280

Leu Leu Lys Ala Ala Leu Ile Ala Gly Ala Ala Asp Ile Gly Leu Gly
    285                 290                 295

Tyr Pro Asn Gly Asn Gln Gly Trp Gly Arg Val Thr Leu Asp Lys Ser
300                 305                 310                 315

Leu Asn Val Ala Tyr Val Asn Glu Ser Ser Ser Leu Ser Thr Ser Gln
                320                 325                 330
```

```
Lys Ala Thr Tyr Ser Phe Thr Ala Thr Ala Gly Lys Pro Leu Lys Ile
            335                 340                 345

Ser Leu Val Trp Ser Asp Ala Pro Ala Ser Thr Thr Ala Ser Val Thr
        350                 355                 360

Leu Val Asn Asp Leu Asp Leu Val Ile Thr Ala Pro Asn Gly Thr Gln
    365                 370                 375

Tyr Val Gly Asn Asp Phe Thr Ser Pro Tyr Asn Asp Asn Trp Asp Gly
380                 385                 390                 395

Arg Asn Asn Val Glu Asn Val Phe Ile Asn Ala Pro Gln Ser Gly Thr
                400                 405                 410

Tyr Thr Ile Glu Val Gln Ala Tyr Asn Val Pro Val Gly Pro Gln Thr
            415                 420                 425

Phe Ser Leu Ala Ile Val Asn
        430

<210> SEQ ID NO 3
<211> LENGTH: 47
<212> TYPE: DNA
<213> ORGANISM: Artificial
<220> FEATURE:
<223> OTHER INFORMATION: Oligonucleotide as PCR primer designed from
      nucleotide sequence of the KP43 protease gene in Bacillus sp.
      KSM-KP43 with the SD sequence and a insertion of the BamHI
      restriction site at the 5'-end

<400> SEQUENCE: 3
aaatggatcc gtgaggaggg aaccgaatga gaaagaagaa aaaggtg                 47

<210> SEQ ID NO 4
<211> LENGTH: 36
<212> TYPE: DNA
<213> ORGANISM: Artificial
<220> FEATURE:
<223> OTHER INFORMATION: Oligonucleotide as PCR primer designed from
      nucleotide sequence of the downstream region of the KP43 protease
      gene in Bacillus sp. KSM-KP43 with a insertion of the XbaI
      restriction site at the 5'-end

<400> SEQUENCE: 4
atattctaga cgattaccat attaattcct ctaccc                             36

<210> SEQ ID NO 5
<211> LENGTH: 19
<212> TYPE: DNA
<213> ORGANISM: Artificial
<220> FEATURE:
<223> OTHER INFORMATION: Oligonucleotide as PCR primer designed from
      the nucleotide sequence of Bacillus sp. KSM-KP43 gene, KP43
      protease gene

<400> SEQUENCE: 5
gacaattcca cgcgcgacg                                                19

<210> SEQ ID NO 6
<211> LENGTH: 26
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 6
cgtggaattg tccaagcgga tgtggc                                        26
```

<210> SEQ ID NO 7
<211> LENGTH: 19
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 7
cccgcggaag gcttcatgc                                              19

<210> SEQ ID NO 8
<211> LENGTH: 32
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 8
gccttccgcg ggcaaattac tgcattatat gc                               32

<210> SEQ ID NO 9
<211> LENGTH: 19
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 9
cccaaagctt gggcggagg                                              19

<210> SEQ ID NO 10
<211> LENGTH: 31
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 10
cccaagcttt gggaaatatg cggacaatat c                                31

<210> SEQ ID NO 11
<211> LENGTH: 31
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 11
cccaagcttt gggcgctatg cggacaatat c                                31

<210> SEQ ID NO 12
<211> LENGTH: 19
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

```
<400> SEQUENCE: 12
tgtcggccca cgtgaagag                                               19

<210> SEQ ID NO 13
<211> LENGTH: 27
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 13
cgtgggccga caagggatgg acggatc                                      27

<210> SEQ ID NO 14
<211> LENGTH: 27
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 14
cgtgggccga caaacgatgg acggatc                                      27

<210> SEQ ID NO 15
<211> LENGTH: 27
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 15
cgtgggccga cacaggatgg acggatc                                      27

<210> SEQ ID NO 16
<211> LENGTH: 21
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 16
cggtgcaaga gaggatcttg c                                            21

<210> SEQ ID NO 17
<211> LENGTH: 30
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 17
tctcttgcac cgaattcctc cttctgggcg                                   30

<210> SEQ ID NO 18
<211> LENGTH: 50
<212> TYPE: DNA
<213> ORGANISM: Artificial
<220> FEATURE:
```

-continued

<223> OTHER INFORMATION: Oligonucleotide as PCR primer designed from the
    nucleotide sequence of Bacillus sp. KSM-KP43 gene, KP43 protease
    gene

<400> SEQUENCE: 18
tctcttgcac cggattcctc cttctgggcg aaccataaca gtaaatatgc        50

<210> SEQ ID NO 19
<211> LENGTH: 22
<212> TYPE: DNA
<213> ORGANISM: Artificial
<220> FEATURE:
<223> OTHER INFORMATION: Oligonucleotide as PCR primer designed from the
    nucleotide sequence of Bacillus sp. KSM-KP43 gene, KP43 protease
    gene

<400> SEQUENCE: 19
tggtgtgatg cctctgtttt tc        22

<210> SEQ ID NO 20
<211> LENGTH: 35
<212> TYPE: DNA
<213> ORGANISM: Artificial
<220> FEATURE:
<223> OTHER INFORMATION: Oligonucleotide as PCR primer designed from the
    nucleotide sequence of Bacillus sp. KSM-KP43 gene, KP43 protease
    gene

<400> SEQUENCE: 20
cagaggcatc acaccaaggc cttctctatt aaaag        35

<210> SEQ ID NO 21
<211> LENGTH: 21
<212> TYPE: DNA
<213> ORGANISM: Artificial
<220> FEATURE:
<223> OTHER INFORMATION: Oligonucleotide as PCR primer designed from the
    nucleotide sequence of Bacillus sp. KSM-KP43 gene, KP43 protease
    gene

<400> SEQUENCE: 21
caatgtcact cgtccccatc c        21

<210> SEQ ID NO 22
<211> LENGTH: 28
<212> TYPE: DNA
<213> ORGANISM: Artificial
<220> FEATURE:
<223> OTHER INFORMATION: Oligonucleotide as PCR primer designed from the
    nucleotide sequence of Bacillus sp. KSM-KP43 gene, KP43 protease
    gene

<400> SEQUENCE: 22
cgagtgacat tgaataaatc cctgaacg        28

<210> SEQ ID NO 23
<211> LENGTH: 22
<212> TYPE: DNA
<213> ORGANISM: Artificial
<220> FEATURE:
<223> OTHER INFORMATION: Oligonucleotide as PCR primer designed from the
    nucleotide sequence of Bacillus sp. KSM-KP43 gene, KP43 protease
    gene

<400> SEQUENCE: 23
tgtgccattt ggagcggtaa tg        22

<210> SEQ ID NO 24

```
<211> LENGTH: 30
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 24
ccaaatggca caaagtatgt aggaaatgac                                        30

<210> SEQ ID NO 25
<211> LENGTH: 30
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 25
ccaaatggca caaggtatgt aggaaatgac                                        30

<210> SEQ ID NO 26
<211> LENGTH: 30
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 26
ccaaatggca cagattatgt aggaaatgac                                        30

<210> SEQ ID NO 27
<211> LENGTH: 30
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 27
ccaaatggca cagagtatgt aggaaatgac                                        30

<210> SEQ ID NO 28
<211> LENGTH: 19
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene

<400> SEQUENCE: 28
ctgtggtcca accggtacg                                                    19

<210> SEQ ID NO 29
<211> LENGTH: 27
<212> TYPE: DNA
<213> ORGANISM: Artificial
<220> FEATURE:
<223> OTHER INFORMATION: Oligonucleotide as PCR primer designed from the
      nucleotide sequence of Bacillus sp. KSM-KP43 gene, KP43 protease
      gene
```

```
<400> SEQUENCE: 29
ggttggacca cagagattct cgttggc                                    27
```

The invention claimed is:

1. A purified alkaline protease, the amino acid sequence of which consists of an amino acid sequence that has 95% or more homology to that of SEQ ID NO:2, and in which the amino acid at the position corresponding to SEQ ID NO:2 position 194 is arginine or lysine.

2. The purified alkaline protease of claim 1, wherein said sequence has 96% or more homology to that of SEQ ID NO:2, and in which the amino acid at the position corresponding to SEQ ID NO:2 position 194 is arginine or lysine.

3. The purified alkaline protease of claim 1, wherein said sequence has 97% or more homology to that of SEQ ID NO:2, and in which the amino acid at the position corresponding to SEQ ID NO:2 position 194 is arginine or lysine.

4. The purified alkaline protease of claim 1, wherein said sequence has 98% or more homology to that of SEQ ID NO:2, and in which the amino acid at the position corresponding to SEQ ID NO:2 position 194 is arginine or lysine.

5. The purified alkaline protease of claim 1, wherein said sequence has 99% or more homology to that of SEQ ID NO:2, and in which the amino acid at the position corresponding to SEQ ID NO:2 position 194 is arginine or lysine.

6. The purified alkaline protease of claim 1, wherein said sequence is that of SEQ ID NO:2, except that the amino acid at SEQ ID NO:2 position 194 is arginine or lysine.

7. A purified alkaline protease, the amino acid sequence of which consists of the amino acid sequence of amino acids 1 to 434 of SEQ ID NO:2, except that the amino acid at SEQ ID NO:2 position 194 is arginine or lysine.

8. The purified alkaline protease of any one of claims 1-5, wherein the amino acid at the position corresponding to SEQ ID NO:2 position 194 is arginine.

9. The purified alkaline protease of any one of claims 1-5, wherein the amino acid at the position corresponding to SEQ ID NO:2 position 194 is lysine.

10. The purified alkaline protease of claim 6 or claim 7, wherein the amino acid at SEQ ID NO:2 position 194 is arginine.

11. The purified alkaline protease of claim 6 or claim 7, wherein the amino acid at SEQ ID NO:2 position 194 is lysine.

* * * * *